United States Patent [19]

Darrah et al.

[11] Patent Number: 4,842,410

[45] Date of Patent: Jun. 27, 1989

[54] APPARATUS AND METHOD UTILIZING INTERFERENCE FRINGES TO DETERMINE THE THERMAL STABILITY OF A LIQUID

[75] Inventors: Shirley D. Darrah, Needham; Thomas G. DiGiusseppe, Danvers; Edward P. Marram, Newton Centre, all of Mass.; Richard A. Kamin; Clarence Nowack, both of Churchville, Pa.; Rolf Steendal, Natick, Mass.

[73] Assignees: Geo-Centers, Inc., Newton Ctr., Mass.; United States of America, Washington, D.C.

[21] Appl. No.: 35,465

[22] Filed: Apr. 7, 1987

Related U.S. Application Data

[63] Continuation-in-part of Ser. No. 922,900, Oct. 24, 1986, abandoned.

[51] Int. Cl.$^4$ .............................................. G01B 9/02
[52] U.S. Cl. .................................. 356/357; 356/345; 356/355
[58] Field of Search .................. 356/345, 355, 357

[56] References Cited

U.S. PATENT DOCUMENTS

| | | | |
|---|---|---|---|
| 3,319,515 | 5/1967 | Flournoy | 88/14 |
| 3,861,804 | 1/1975 | Lehmbeck | 356/357 |
| 4,293,224 | 10/1981 | Gaston et al. | 356/357 |
| 4,377,343 | 3/1983 | Monson | 356/357 |
| 4,558,950 | 12/1985 | Ulrich et al. | 356/345 |

OTHER PUBLICATIONS

"In-Situ et al., Real-Time Thin Film Refractive Index and Thickness Monitor, " G. H. Hewig et al., IBM Technical Disclosure Bulletin, vol. 25, No. 1, Jun. 1982, pp. 436–438.

Primary Examiner—Vincent P. McGraw
Assistant Examiner—S. A. Turner
Attorney, Agent, or Firm—Wolf, Greenfield & Sacks

[57] ABSTRACT

In a method of evaluating the thermal stability of hydrocarbon liquid fuels, the fuel flows over a heated tube that causes the fuel to decompose and deposit a residue as a film on the surface of the heated tube. The thickness of that residue film is a measure of the fuel's thermal stability. To measure the film's thickness, the film is illuminated with light that is substantially monochromatic. The light reflected from the surface of the heater tube interferes with the light reflected from the overlying surface of the residue film on that tube and thereby causes variations in the intensity of the reflected light. Those variations in intensity of the reflected light are detected to obtain a measure of the thickness of the film. In one embodiment of the invention, the heated tube is situated in an enclosed housing through which the fuel is caused to flow and the thickness measurement is made while the film builds up on the heated tube. In another embodiment of the invention, the film on the heater tube is evaluated after the complete thickness has been deposited.

14 Claims, 4 Drawing Sheets

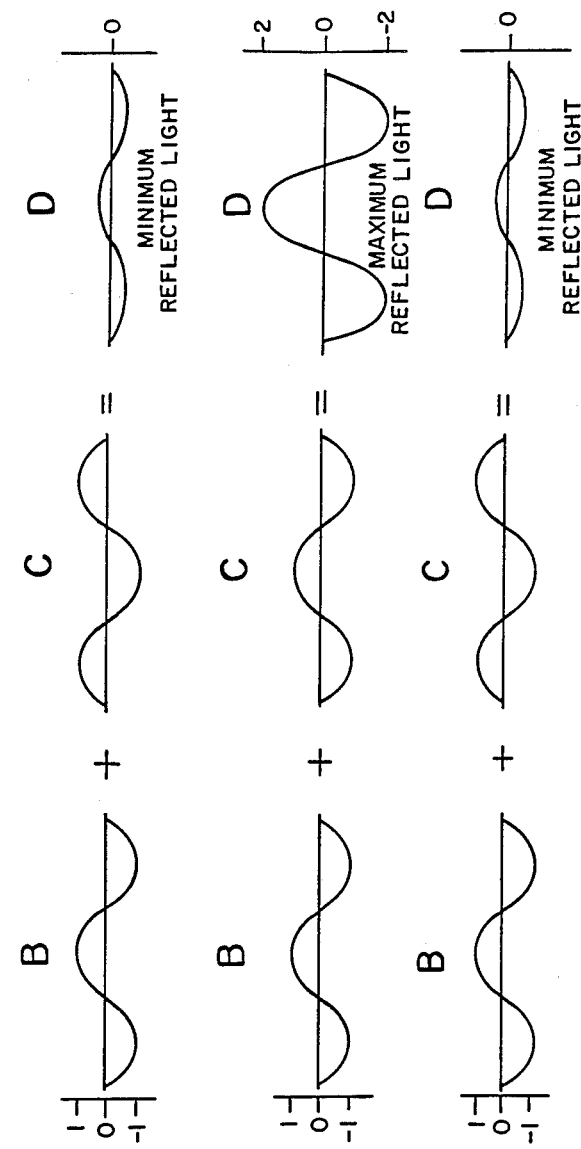

APPARATUS AND METHOD UTILIZING INTERFERENCE FRINGES TO DETERMINE THE THERMAL STABILITY OF A LIQUID

U.S. GOVERNMENT RIGHTS IN THE INVENTION

This invention was made jointly by two employees of the Naval Air Propulsion Center of Trenton, N.J. and four employees of Geo-Centers, Inc. The four Geo-Centers employees, at the time the invention was made, were in the performance of work under Naval Research Laboratory's contract N00014-84-C-2345 with Geo-Centers. The United States of America has certain rights in the invention arising out of that contract, including a nonexclusive, nontransferable, irrevocable, paid-up license to practice the invention or have it practiced for or on behalf of the United States throughout the world.

RELATED APPLICATION

This application is a continuation-in-part of our application, Ser. No. 922,900, now abandoned, which was filed in the United States Patent And Trademark Office on Oct. 24, 1986.

FIELD OF THE INVENTION

This invention relates in general to the evaluation of the thermal stability of fuels, lubricants, and other hydrocarbon liquids. More particularly the invention pertains to the evaluation of the thermal stability of liquids by measurement of the thickness of the film deposited by the liquid on a heated metal surface in a test run. The invention resides in an arrangement which enables the thickness of the film deposited on the heated metal surface to be continuously measured as that film becomes progressively thicker during the test run and in the method of making the measurements.

BACKGROUND OF THE INVENTION

Because of thermal instability, fuels used for jet propulsion, tend, when heated, to leave a residue that builds up and clogs the orifices, nozzles, and conduits leading to the combustion chamber. Consequently, means have been devised for rating the thermal stability of the jet fuels.

In an earlier method for evaluating the thermal stability of jet fuel, the fuel was passed by a heated metal tube at a constant rate for a specified period of time. To keep the fuel in its liquid state, the fuel was under pressure during the test run. After the test run, the metal tube was removed from the test apparatus and the film deposited on the tube was rated by comparison of the film's color with an ASTM color standard.

In another method for evaluation of the jet fuel's thermal stability, the metal tube, after the test run, is removed from the apparatus and the film deposited on the tube is rated with an instrument known as a "tube deposit rater". To those familiar with the evaluation of jet fuel properties, the tube deposit rater is familiarly referred to as the "TDR". In the tube deposit rater, visible light is directed at the film deposit on the metal tube and the relative intensity of the reflected light is indicated on a calibrated meter. The meter readings range between 0 and 50 and the readings are inversely related to the intensity of the reflected light. The less the intensity, the higher the reading. When rating the thermal stability of a jet fuel, the metal tube, after the test run, is placed in the TDR and the length of the tube is scanned until a position is located at which the maximum meter reading is obtained. The reading at the position is then the rating for the fuel. The basis for that procedure is the assumption that the reflected light intensity decreases monotonically with increasing film thickness so that the rating corresponds to film thickness. The conventional TDR employs a photo detector whose region of sensitivity to the light spectrum extends from 400 to 750 nm (nanometers) with maximum sensitivity at 550 nm. That region coincides with the region where large polycyclic aromatic compounds undergo transitions by the absorption of light. It is believed that those molecules are produced in the thermal oxidation of hydrocarbon fuels and that because of their low solubility the compounds form a deposit on the heater tube. Consequently, it was reasoned that, the thicker the deposit, the more light was absorbed by the large polycyclic aromatic molecules and the less light was reflected so that the intensity of the reflected light decreased in direct relation to the thickness of the deposit. However, evidence has accumulated which indicates that ratings made with the conventional TDR are inaccurate because those ratings do not correlate with data obtained in the testing of jet engines.

THE INVENTION

Underlying this invention is the discovery that the cause of the inaccuracy in the TDR ratings is interference with the light reflected from the surface of the metal tube by light reflected from the outer surface of the film deposit on that tube—that is, the realization that some of the light directed at the metal tube is reflected at the outer surface of the film, that some of the light passes into the film and is reflected at the surface of the metal tube beneath the film, and that the two reflections result in the light reflected from one of those two surfaces interfering with the light reflected from the other of those surfaces.

The preferred embodiment of the invention utilizes a fiber optic light transmission probe to illuminate the metal heater tube in situ while a test run is made and to collect the reflected light while the test is in progress to enable continuous measurements of the thickness of the film to be made contemporaneously with the deposition of the film on the heated metal tube (i.e. in the terminology of the scientist, the measurements are made "in real time"). With this embodiment, changes in film thickness can be continuously monitored while the jet fuel thermal stability evaluation test is in progress whereby an accurate determination of the thickness of the film formed at any desired time in the test is obtainable. The preferred source of illumination is a laser that provides coherent light of a selected wave length to the probe. However, light emitting diodes, arc lamps, and other light sources can be used in place of or in addition to a laser. Because the metal heater tube has a known thermal profile or its thermal profile can easily be established, this embodiment enables an array of fiber optic probes to be mounted along the heater tube housing so that the rate of deposit of the film on the heated tube at different temperatures along that tube can be simultaneously obtained in a single test run Another embodiment of the invention, known as the "off-line" TDR, enables specimen heater tubes to be subjected to test runs without making real time measurements. After completion of the test runs, the heater tubes are removed and transferred to the off-line TDR where the thickness of the deposit on each heater tube is measured.

THE DRAWINGS

Figure 3:
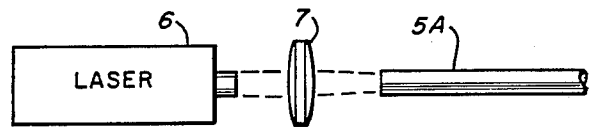

FIG. 3 schematically depicts the focusing of light from a laser upon the input end of the core fiber optic of a probe.

Figure 4:
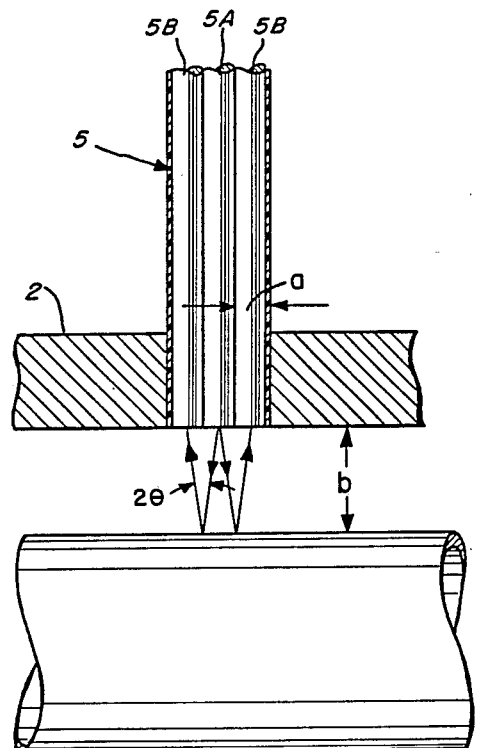

FIG. 4 shows the mounting of the fiber optic probe flush with the inner wall of the housing and the disposition of that probe in relation to the heater tube.

FIG. 5 illustrates the phenomenon of light interference with a film thickness of one quarter the wavelength of the incident light.

FIG. 6 illustrates the phenomenon of light interference with a film thickness of one half the wavelength of the incident light.

Figure 8:
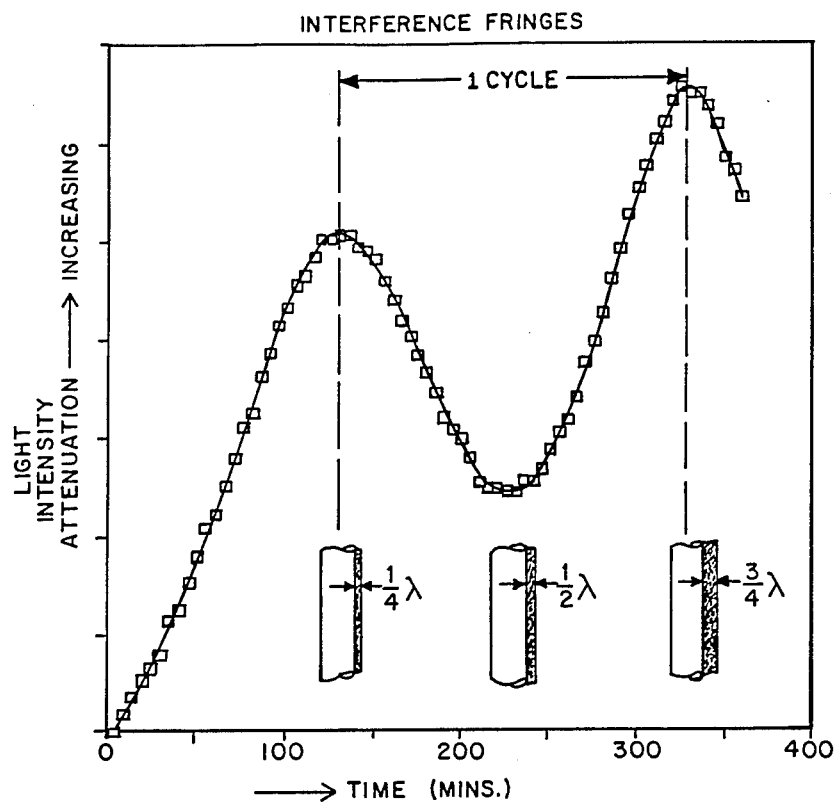

FIG. 7 illustrates the phenomenon of light interference with a film thickness of three quarters the wavelength of the incident light FIG. 8 is a graph showing the maxima and minima encountered as the film deposit builds up during a test run.

Figure 9:
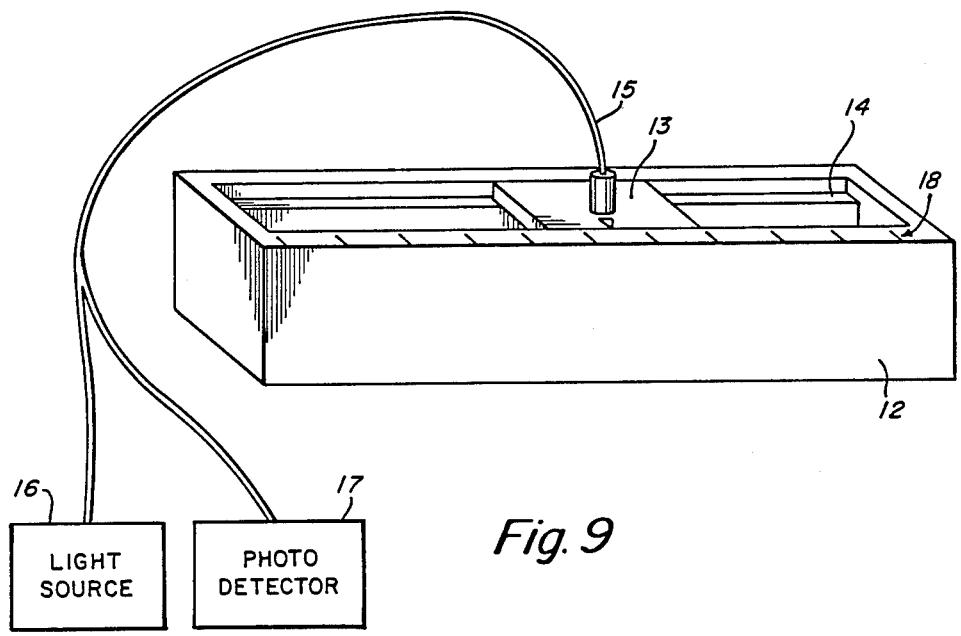

FIG. 9 shows an "off-line" embodiment of the invention in which the thickness of the heater tube's film deposit is measured after the entire film has been deposited on the tube.

DETAILED DESCRIPTION OF PREFERRED EMBODIMENT OF THE INVENTION

Figure 1:
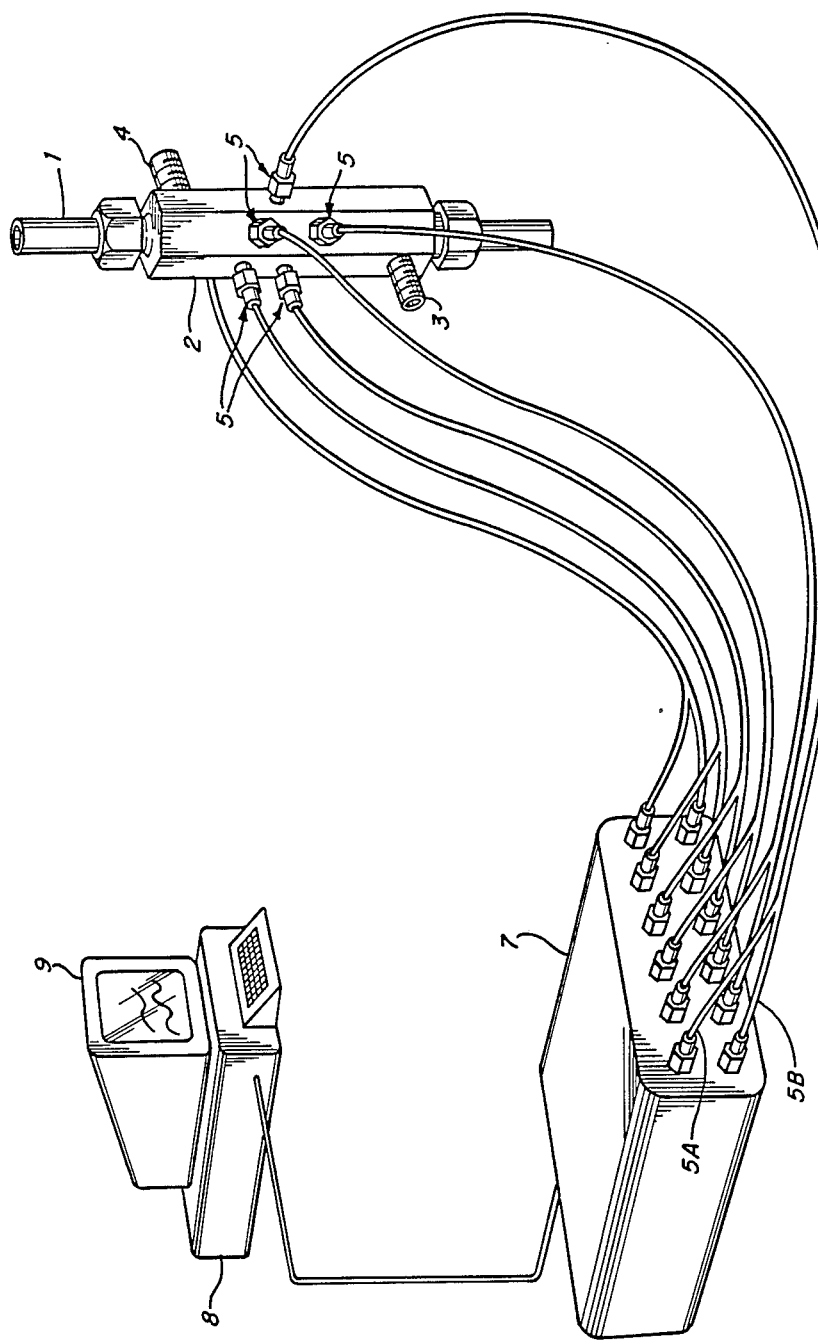
FIG. 1 is a schematic depiction of the preferred embodiment of the invention.

Referring now to the drawings, FIG. 1 shows the scheme of the preferred embodiment of the invention. In that schematic depiction, metal heater tube 1 extends into a housing 2 having an inlet port 3 and an outlet port 4. The housing 2 provides an annular chamber around the metal tube 1. In a test run, the housing is upright and the jet fuel enters the bottom of the chamber from the inlet port 3, flows upwardly through the chamber at a constant rate, and in so doing is thermally destabilized and deposits a residue that forms a film on the hot surface of the heated tube 1. The jet fuel then exits from the top of the chamber through the outlet port 4. For a typical jet fuel, the peak temperature of the heater tube is in the 400° to 600° F. range. To keep the fuel in its liquid state in its passage through the housing, the fuel in maintained under pressure.

The metal tube 1 is internally heated by an electrical resistance element and the tube has a smooth outer surface which is light reflective. Mounted on the housing is an array of fiber optic probes. The probes 5 of that array are spaced along the length of the heater tube 1. Each probe 5, as shown in cross-section in FIG. 2, has a core fiber optic 5A around which are disposed receptor fiber optics 5B. Coherent light from a laser 6, shown in FIG. 3, is focused by a lens 7 upon the input end of core fiber optic 5A. That light propagates along the fiber optic to its other end which is flush with the inner wall of housing 2. Preferable, the wavelength of the light emitted by the laser is 0.880 microns. However, light of other wavelengths can be used. Preferably, the light is monochromatic (i.e., of one wavelength) or has a narrow range of wavelengths centered about a principal wavelength. One criterion in selecting light of a specific wavelength is the transparency of the film deposit to that light. A wavelength should be selected to which the film is highly transparent and which permits the requisite accuracy and range to be realized The wavelength of the light affects the accuracy of measurement and the shorter wavelength enable higher accuracies to be realized. However, the film tends to become more opaque as the wavelength drops into the ultraviolet region of the spectrum.

The fiber optic probe 5, as schematically shown in the enlarged view of FIG. 4, has one end extending into the wall of housing 2 and ending flush with the interior wall of that housing. For simplicity, the seals used to prevent leakage through and around the probe have been omitted in FIG. 4, as have the connectors used to secure the probe to the housing. In FIG. 4, the diameter of the fiber optic is indicated by the "a" dimension. The distance b from the end of the fiber optic probe to the adjacent surface of the heater tube 1 is large compared to the minute thickness of the film that builds up on the heater tube during a test run. The light emitted from core fiber optic 5A emerges as a cone and therefore some of that light diverges from normal and is reflected at an angle $\theta$ from the normal to the surface of the heater tube and is incident upon the ends of receptor fiber optics 5B. Some of the light emitted from core fiber optic 5A is reflected from the outer surface of the film deposited on the heater tube during the test run. Because the thickness of that film is small compared to the distance b and to the diameter a of the 5B fiber optics, the film thickness has an inappreciable effect on the angle at which the light is reflected from the film's surface. Consequently, both the light reflected from the surface of the heater tube and the light reflected from the surface of the film deposit are received by the ends of receptor fiber optics 5B and propagate through those fiber optics to light detectors situated in the cabinet 7 shown in FIG. 1. The light detectors detect the intensity of the light emitted from the receptor fiber optics 5B and the output signals of the light detectors are transmitted to a computer 8 which controls the visual display of a monitor 9.

The phenomenon of interference between light reflected from the film's surface and light reflected from the surface of the heater tube can be better understood from a consideration of FIGS. 5, 6, and 7. For purposes of exposition, only coherent light of a single wavelength is here considered. In FIG. 5A, the film thickness on the heater tube is $\frac{1}{4}\lambda$. The light reflected from the heater tube's surface, when it passes out of the film, is 180° out of phase with the light reflected from the film's surface, as shown in FIGS. 5B and 5C, and thus the light waves tend to cancel one another. Inasmuch as the amplitude of the light reflected from the heater tube surface is somewhat reduced by scattering and absorption in its passage through the film layer, complete cancellation does not occur even if half the incident light enters the film. However, the intensity of the light entering the receptor fiber optics is at a minimum.

In FIG. 6, the thickness of the film indicated in FIG. 6A is $\frac{1}{2}\lambda$. The light passing through that film and reflected from the surface of the heater tube, emerges from the film in phase with the light reflected at the film's surface. The two waves, shown in FIGS. 6B and 6C, are additive and consequently, the light received by receptor fiber optics 5B is at maximum intensity.

In FIG. 7, the thickness of the film is indicated in FIG. 7A is $\frac{3}{4}\lambda$. Consequently, the light passing through that film and reflected from the heater tube's surface emerges from the film 180° out of phase with the light reflected at the film's surface. The two waves, shown in FIGS. 7B and 7C, interfere with one another and partial cancellation results. The intensity of the light received by receptor fiber optics 5B is therefore greatly reduced.

From the foregoing, it can be appreciated that as the thickness of the film deposited on the heater tube builds up during the test run, the light received from the receptor fiber optics varies in intensity and passes alternately through minimum and maximum intensities. Those minimum and maximum intensities correspond to the fringe pattern observed as a phenomenon of light interference. By counting the minimum and and maximum intensities, a measurement of the thickness of the film deposit on the heater tube is obtained. Inasmuch as the thickness of that deposit is related to the thermal stability of the jet fuel, an evaluation of that property is obtained.

Correct interpretation of the light interference phenomenon allows the quantitative determination of the film thickness. The thickness d of the film is $$d = \frac{m\lambda}{2n \cos \theta}$$

where
  m is the number of oscillations in light intensity,
  $\lambda$ is the wavelength of the light,
  n is the refractive index of the film,
  $\theta$ is the angle at which the light propagates through the film relative to the normal to the film's surface.

The adsorption coefficient of the film deposit may be derived by observing the trend in the attenuation of the intensity of the reflected light.

This can be better appreciated from a consideration of the FIG. 8 graph in which attenuation of light intensity is plotted along the ordinate and time, in minutes, of the test run is plotted along the abscissa. It can be seen that peak intensity is attained when the film thickness is at $\frac{1}{2}\lambda$ and that minimum intensity is attained when the film thickness is $\frac{1}{4}$ and $\frac{3}{4}\lambda$. It is evident from the graph that there is a trend toward greater attenuation in light intensity with increasing film thickness. The thickness of the film is proportional to $\frac{1}{2}\lambda$ multiplied by the number of cycles in the light intensity variation.

For purposes of continuous measurement, an approximation of the film's refractive index and of the angle $\theta$ is used. After the test run, the accuracy of the approximation may be determined by removing the heater tube from the housing and establishing the film's refractive index by well-known procedures.

Figure 2:
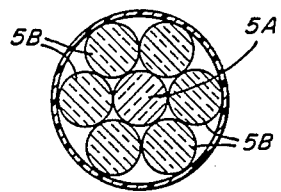
FIG. 2 is a cross-sectional view showing the interior arrangement of the optical fibers of a probe.

The preferred construction of the probe, as shown in cross-section in FIG. 2, is a fiber bundle having a core fiber that conducts light from a laser source to the heater tube and six receptor fibers that conduct the reflected light to a light detector. Obviously, other probe configurations can be employed in which the number of fibers and their disposition in the bundle can be varied.

FIG. 9 of the drawings schematically depicts an "off-line" embodiment of the invention for measuring the thickness of the deposit on the heater tube after a run has been completed in which the entire film was deposited on that tube. That is, in the "off-line" technique, the thickness of the heater tube's deposit is measured sometime after the complete thickness of the fuel residue has been deposited on the heater tube. The residue coated tube provides a permanent record of the test and an advantage of the "off-line" technique is that the profile of deposit thickness along the tube can be determined at any time subsequent to the run.

In the "off-line" technique, the thickness measurement is made after the entire film has been deposited on the heater tube. The measurement is made by scanning the entire tube, beginning at the end which was adjacent to the fuel inlet. The two ends of the heater tube, it is known, act as heat sinks and consequently the fuel is heated to its maximum, temperature at some position intermediate those ends. At the fuel inlet end of the heater tube, no residue is deposited during the test run because the entering fuel is not then heated sufficiently by the heater tube to thermally decompose. In the test runs, it was found that the thickness of the deposit gradually increased along the tube until a site was reached on the heater tube at which the film thickness was greatest and that the deposit thickness then gradually decreased over the remainder of the tube as the fuel outlet end of the tube was approached. It is known that the fuel becomes hotter as it flows along the heater tube in a test run and it is assumed that the film deposit attains its greatest thickness at the position along the heater tube where the fuel reaches the temperature at which maximum thermal decomposition occurs. The gradual decrease in thickness which occurs thereafter in the film deposit is attributed to a tapering off of the rate of thermal decomposition until virtually no thermal decomposition occurs at the fuel outlet. When the tube is scanned from either end to the site of maximum film thickness, the reflected light intensity varies and passes alternately through minimum and maximum intensities. The same number of minima and maxima are observed on both sides of the site of maximum film thickness. Those minimum and maximum intensities correspond to the fringe pattern observed as a phenomenon of light interference. The thickness of the film at any selected position on the tube can be determined by counting the number of minimum and maximum intensities detected in scanning from the end of the tube to that position. The same result is obtained when the scan direction is reversed—that is, when the scan direction is from the selected position to the end of the tube. The number of minimum and maximum intensities counted in the scan equals the number counted at that selected position at the end of the test run in the in-situ measurement.

The "off-line" instrument, shown in FIG. 9, employs a housing 12 in which the residue bearing heater tube is placed in a horizontal position. A carriage 13 is arranged to slide along a slot 14 in the housing. Mounted on carriage 13 is a probe 15 having a fiber optic bundle. Preferably the probe is on the kind shown in FIG. 2 in which the bundle has receptor fibers disposed around a core fiber. The core fiber of probe 15 transmits light from source 16 to the interior of the housing. The receptor fibers of probe 15 transmit reflected light to photodetector 17. Because of the narrow light acceptance cone of the receptor fibers, the carriage itself is adequate to shield the receptor fibers from ambient light. By sliding the carriage along the length of the housing, measurements can be made of the thickness of the deposit from one end of the heater tube to the other. To enable that to be accomplished, the heater tube is disposed in the housing so that it extends lengthwise with respect to the path of travel of the carriage. To enable a determination to be easily made of the position of the carriage along its path of travel, the carriage is provided with a pointer that moves along a graduated scale 18 on the housing.

In both the in-situ and "off-line" measurements, the choice of wavelength of the source light is governed by the thickness of the film to be measured. For thin films, short wavelength light is most appropriate because the reflected light intensity changes more quickly that it does with longer wavelength light. Thus, a more accurate measure of the film's thickness is obtained. However, shorted wavelength light is more strongly absorbed by the film than is longer wavelength light. This leads to decreasing amplitudes of the maxima and minima of the reflected light intensity as the film thickness increases. Therefore, longer wavelength light is more appropriate for the measurement of thicker films. For this reason, it is advantageous to provide optional light sources (and optional detectors) in the measuring device or to utilize beam splitters to multiplex light of two different wavelengths through the fibers of the probe to increase the dynamic range of the measurement device.

Obvious modifications of the invention will be evident to those persons skilled in the art of measuring thickness to accuracies in the order of a wavelength of visible light. For example, where a light source is specified herein as having a single wavelength or a small range of wavelengths, it is evident that a photo detector can be arranged to be responsive to the single wavelength or the narrow range of wavelengths and that a light source can then be employed having a broad spectrum of light. As another example of an obvious modification, in the FIG. 9 embodiment, it is evident that the carriage can be stationary and that the heater tube in the housing can be arranged to be moved relative to the stationary carriage. To a skilled person, it is evident that what is required is relative motion and that there are a number of obvious ways to produce that relative motion.

In view of the modification of the invention that are obvious to those persons skilled in making measurements that are accurate to one wavelength of visible light, it is not intended that the invention be restricted to the embodiments here disclosed. Rather, it is intended that the invention be construed in accordance with the accompanying claims, having due regard for modifications that merely involve the substitution of equivalents or other obvious changes.

We claim:

1. A method of evaluating the thermal stability of a liquid utilizing interference fringes to determine the thickness of a film deposited on a surface of a heated tube by the liquid, said method comprising the steps of:
   (a) illuminating the film deposited on the heated tube with light,
   (b) detecting at a predetermined wavelength the variation in reflected light caused by interference between the light reflected from the surface of the heated tube and light reflected from the film's surface as the film thickness changes over time or space from zero to the measured thickness,
   (c) ascertaining the number of cycles in the variation of the intensity of the reflected light to determine the thickness of the film, and
   (d) determining the thermal stability of the liquid from the film thickness.

2. The method according to claim 1, wherein step (b) is carried out while the film is being deposited on the heated tube and the variation is detected over time at a preselected site on the heated tube.

3. The method according to claim 1, wherein step (b) is carried out after the film has been deposited on the heated tube and the variation is detected over space at a plurality of sites on the heated tube.

4. The method according to claim 1, wherein the illuminating light is of the predetermined wavelength.

5. The method according to claim 4, wherein the predetermined wavelength is one to which the film is substantially transparent.

6. The method according to claim 1, further comprising the step of
selecting the predetermined wavelength based upon the film thickness to be measured, wherein a shorter wavelength is selected for use with thinner films to increase the accuracy of the measurement and a longer wavelength is selected for use with thicker films to increase the amplitude of the intensity.

7. Apparatus for evaluating the thermal stability of a liquid utilizing interference fringes to determine the thickness of a film deposited on a surface of a heated tube by the liquid, said apparatus comprising:
   (a) a housing providing a closed chamber with an inlet port and an outlet port, wherein the liquid to be evaluated is caused to flow through the chamber from the inlet port to the outlet port,
   (b) a tube disposed in the chamber,
   (c) means for heating the tube, wherein the liquid deposits a film on a surface of the tube,
   (d) means for transmitting an illuminating light to the surface of the heated tube,
   (e) means for transmitting light reflected from the surface of the heated tube,
   (f) means for detecting at a predetermined wavelength the variation caused by interference between the light reflected from the film and the light reflected from the underlying surface of the heated tube, and
   (g) means for ascertaining the number of cycles of the variation in the intensity of the reflected light to determine over time the thickness of the film at a preselected site on the heated tube as it varies from zero to the measured thickness.

8. The apparatus of claim 7, wherein the transmitting means for the illuminating and reflected light comprises fiber optic means.

9. The apparatus of claim 8, wherein the fiber optic means comprises a plurality of receptor optical fibers for transmitting the reflected light radially arranged around an illuminating optical fiber for transmitting the illuminating light.

10. The apparatus of claim 9, wherein the thickness of the film to be measured is small compared to each of: the distances from the ends of the illuminating and receptor fiber optic means to the tube, and the diameter of the receptor fiber optic means.

11. The apparatus of claim 7, further comprising a light source for providing an illuminating light at the predetermined wavelength.

12. The apparatus of claim 11, wherein the predetermined wavelength is one to which the film is substantially transparent.

13. The apparatus of claim 7, further comprising means for varying the predetermined wavelength wherein a shorter wavelength can be selected for use with thinner films to increase the accuracy of the measurement and a longer wavelength can be selected for use with thicker films to increase the amplitude of the intensity.

14. Apparatus for evaluating the thermal stability of a liquid utilizing interference fringes to determine the thickness of a film deposited on a surface of a heated tube by the liquid, said apparatus comprising
  (a) a heated tube, wherein the liquid to be evaluated is caused to flow over a surface of the heated tube and deposits a film on the surface,
  (b) probe means including means for directing light onto the tube and means for detecting at a predetermined wavelength the variation in reflected light caused by interference between the light reflected from the film and light reflected from the underlying surface of the tube,
  (c) means for effecting relative movement between said probe means and said tube so that said variation is detected over space at a plurality of sites on the tube from a film thickness of zero to the measured value, and
  (d) means for ascertaining the number of cycles of the variation in intensity of the reflected light to determine the measured thickness of the film.

* * * * *